(12) United States Patent
Cho et al.

(10) Patent No.: US 10,427,124 B2
(45) Date of Patent: Oct. 1, 2019

(54) METHODS FOR CONTROLLING ASSEMBLY OF LIPIDS ON A SOLID SUPPORT

(71) Applicant: Nanyang Technological University, Singapore (SG)

(72) Inventors: Nam-Joon Cho, Singapore (SG); Joshua Alexander Jackman, Singapore (SG)

(73) Assignee: Nanyang Technological University, Singapore (SG)

( * ) Notice: Subject to any disclaimer, the term of this patent is extended or adjusted under 35 U.S.C. 154(b) by 487 days.

(21) Appl. No.: 15/023,055

(22) PCT Filed: Sep. 19, 2014

(86) PCT No.: PCT/SG2014/000449
§ 371 (c)(1),
(2) Date: Mar. 18, 2016

(87) PCT Pub. No.: WO2015/041608
PCT Pub. Date: Mar. 26, 2015

(65) Prior Publication Data
US 2016/0228839 A1    Aug. 11, 2016

Related U.S. Application Data

(60) Provisional application No. 61/879,914, filed on Sep. 19, 2013.

(51) Int. Cl.
*A61K 9/12* (2006.01)
*B05D 1/00* (2006.01)
(Continued)

(52) U.S. Cl.
CPC ............. *B01J 13/04* (2013.01); *A61K 9/1271* (2013.01); *B05D 1/007* (2013.01); *B05D 3/104* (2013.01);
(Continued)

(58) Field of Classification Search
CPC ............................. A61K 9/1271; B05D 1/007
See application file for complete search history.

(56) References Cited

U.S. PATENT DOCUMENTS

| | | | |
|---|---|---|---|
| 8,211,712 B2 * | 7/2012 | Cho | B82Y 5/00 436/518 |
| 2004/0208921 A1 * | 10/2004 | Ho | A61K 9/127 424/450 |

(Continued)

FOREIGN PATENT DOCUMENTS

| WO | WO 1996/010178 A1 | 4/1996 |
|---|---|---|
| WO | WO 2001/026800 A1 | 4/2001 |
| WO | WO 2002/071944 A1 | 9/2002 |

OTHER PUBLICATIONS

Nollert et al. Lipid Vesicle Adsorption versus Formation of Planar Bilayers on Solid Surfaces. Biophysical Journal Vo. 69 Oct. 1995 pp. 1447-1455 (Year: 1995).*

(Continued)

*Primary Examiner* — Cachet I Proctor
(74) *Attorney, Agent, or Firm* — Alston & Bird LLP

(57) ABSTRACT

The invention relates to a method of controlling adsorption of lipid molecules onto a solid support by tuning the steric-hydration force of the lipid vesicles and the surface of the solid support, such that the solid support either has a stabilized lipid bilayer adsorbed thereon or is resistant to adsorption of lipid molecules.

19 Claims, 6 Drawing Sheets

(51) Int. Cl.
  *B01J 13/04* (2006.01)
  *G01N 33/543* (2006.01)
  *A61K 9/127* (2006.01)
  *B05D 3/10* (2006.01)
  *B05D 3/14* (2006.01)
(52) U.S. Cl.
  CPC ....... *B05D 3/142* (2013.01); *G01N 33/54393* (2013.01)

(56) References Cited

U.S. PATENT DOCUMENTS

| | | | | |
|---|---|---|---|---|
| 2005/0142114 A1* | 6/2005 | Gieseler | ................. | A61K 9/127 424/93.2 |
| 2006/0014013 A1* | 1/2006 | Saavedra | ................ | A61L 27/34 428/338 |
| 2009/0286435 A1* | 11/2009 | Badyal | ................. | A61L 33/064 442/59 |
| 2013/0273561 A1* | 10/2013 | Walker | ............. | G01N 33/54346 435/7.2 |
| 2014/0112979 A1* | 4/2014 | Andreasen | ........... | A61K 9/1277 424/450 |

OTHER PUBLICATIONS

Anderson et al. Formation of Supported Bilayers on Silica Substrates. Langmuir 2009. vol. 25 (12) pp. 6997-7005 (Year: 2009).*
Ahmed et al. Hydration Repulsion Effects of the Formation of Supported Lipid Bylayers. Soft Matter. 7(5):1936-1947. 2011 (Year: 2011).*
Berquand, A. et al., *Two-Step Formation of Streptavidin-Supported Lipid Bilayers by PEG-Triggered Vesicle Fusion. Fluorescence and Atomic Force Microscopy Characaterization*, Languir 19 (2003) 1700-1707.
Boudard, S. et al., *Controlling the Pathway of Formation of Supported Lipid Bilayers of DMPC by Varying the Sodium Chloride Concentration*, Thin Solid Films 495 (2006) 246-251.
Boxer, S. G., *Molecular Transport and Organization in Supported Lipid Membranes*, Current Opinion in Chemical Biology 4(6) (2000) 704-709.
Castellana, E. T. et al., *Solid Supported Lipid Bilayers: From Biophysical Studies to Sensor Design*, Surface Science Reports 61 (2006) 429-444.
Cha, T. et al., *Formation of Supported Phospholipid Bilayers on Molecular Surfaces: Role of Surface Charge Density and Electrostatic Interaction*, Biophysical Journal, vol. 90 (Feb. 2006) 1270-1274.
Chan, K-H. M. et al., *Model Membrane Systems and Their Applications*, Current Opinion in Chemical Biology 11 (2007) 581-587.
Cho, N-J et al., *Fabrication of a Planar Zwitterionic Lipid Bilayer on Titanium Oxide*, Langmuir 26 (20) (2010) 15706-15710.
Cho, N-J et al., *Quartz Crystal Microbalance With Dissipation Monitoring of Supported Lipid Bilayers on Various Substrates*, Nature Protocols, vol. 5, No. 6 (2010) 1096-1106.
Cho, N-J et al., *pH-Driven Assembly of Various Supported Lipid Platforms: A Comparative Study on Silicon Oxide and Titanium Oxide*, Langmuir 27 (2011) 3739-3748.
Cremer, P. S. et al., *Formation and Spreading of Lipid Bilayers on Planar Glass Supports*, J. Phys. Chem. B 103 (1999) 2554-2559.
Czolkos, I. et al., *Molecular Phospholipid Films on Solid Supports*, Soft Matter 7 (2011) 4562-4576.
Dimitrievski, K., *Influence of Lipid-Bilayer-Associated Molecules on Lipid-Vesicle Adsorption*, Langmuir 26(8) (2010) 5706-5714.
Florin, E. L. et al., *Painted Supported Lipid Membranes*, Biophys. J. vol. 64 (Feb. 1993) 375-383.
Gaede, H. C. et al., *Multinuclear NMR Studies of Single Lipqid Bilayers Supported in Cylindrical Aluminum Oxide Nanopores*, Langmuir 20 (2004) 7711-7719.

Groves, J. T. et al., *Micropatterning Fluid Lipid Bilayers on Solid Supports*, Science, vol. 275 (Jan. 1997) 651-653.
Groves, J. T. et al., *Substrate-Membrane Interactions: Mechanisms for Imposing Patterns on a Fluid Bilayer Membrane*, Langmuir 14 (1998) 3347-3350.
Gulcev, M. D. et al., *Factors Affecting the Behavior and Effectiveness of Phospholipid Bilayer Coatings for Capillary Electrophoeretic Separations of Basic Proteins*, Analytical Chemistry, vol. 80, No. 5 (Mar. 2008) 1806-1812.
Gun'ko, V. M. et al., *Active Site Nature of Pyrogenic Alumina/Silica and Water Bound to Surfaces*, Langmuir 13 (1997) 1529-1544.
Jackman, J. A. et al., *Influence of Osmotic Pressure on Adhesion of Lipid Vesicles to Solid Supports*, Langmuir 29 (2013) 11375-11384.
Jackman, J. A. et al., *Interfacial Binding Dynamics of Bee Venom Phospholipase $A_2$ Investigated By Dynamic Light Scattering and Quartz Crystal Microbalance*, Langmuir 26(6) (2010) 4103-4112.
Johnson, J. M. et al., *Early Steps of Supported Bilayer Formation Probed by Single Vesicle Fluorescence Assays*, Biophysical Journal, vol. 83 (Dec. 2002) 3371-3379.
Keller, C. A. et al., *Surface Specific Kinetics of Lipid Vesicle Adsoprtion Measured With a Quartz Crystal Microbalance*, Biophysical Journal, vol. 75 (Sep. 1998) 1397-1402.
Korgel, B. A. et al., *Vesicle Size Distributions Measured by Flow Field-Flow Fractionation Coupled With Multiangle Light Scattering*, Biophysical Journal, vol. 74 (Jun. 1998) 3264-3272.
Kosmulski, M., *A Literature Survey of the Differences Between the Reported Isoelectric Points and Their Discussion*, Colloids and Surfaces A: Physicochem. Eng. Aspects 222 (2003) 113-118.
MacDonald, R. C. et al., *Small-Volume Extrusion Apparatus for Preparation of Large, Unilamellar Vesicles*, Biochimica et Biophysica Acta, 1061 (1991) 297-303.
Mager, M. D. et al., *Formation and Characterization of Fluid Lipid Bilayers on Alumina*, Langmuir 24 (2008) 12734-12737.
Mayer, L. D. et al., *Vesicles of Variable Sizes Produced by a Rapid Extrusion Procedure*, Biochimica et Biophysica Acta 858 (1986) 161-168.
McConnell, H. M. et al., *Supported Planar Membranes in Studies of Cell-Cell Recognition in the Immune System*, Biochimica et Biophysica Acta 864 (1986) 95-106.
McIntosh, T. J. et al., *Contributions of Hydration and Steric (Entropic) Pressures to the Interactions Between Phosphatidylcholine Bilayers: Experiments With the Subgtel Phase*, Biochemistry 32 (1993) 8374-8384.
Nabika, H. et al., *Tuning the Dynamics and Molecular Disbribution of the Self-Spreading Lipid Bilayer*, Phys. Chem. Chem. Phys., 10 (2008) 2243-2248.
Parikh, A. N. et al., *Materials Science of Supported Lipid Membranes*, MRS Bulletin, vol. 31 (Jul. 2006) 507-512.
Pfeiffer, I. et al., *Formation of Pit-Spanning Phospholipid Bilayers of Nanostructured Silicon Dioxide Surfaces for Studying Bilogical Membrane Events*, Chap. 12, Humana Press, Eds. Weissig et al., vol. 991 (2013) 113-125.
Reimhult, E. et al., *A Multitechnique Study of Liposome Adsorption on Au and Lipid Bilayer Formation on $SiO_2$*, Langmuir 22 (2006) 3313-3319.
Reimhult, E. et al., *Intact Vesicle Adsorption and Supported Biomembrane Formation From Vesicles in Solution: Influence of Surface Chemistry, Vesicle Size, Temperature, and Osmotic Pressure*, Langmuir 19 (2003) 1681-1691.
Reimhult, E. et al., *Temperature Dependence of Formation of a Supported Phospholipid Bilayer from Vesicles on $SiO_2$*, Physical Review E 66 (2002) 4 pages.
Reimhult, E. et al., *Vesicle Adsoprtion on $SiO_2$ and $TiO_2$: Dependence on Vesicle Size*, Journal of Chemical Physics, vol. 117, No. 16 (Oct. 2002) 7401-7404.
Reviakine, I. et al., *Investigating the Properties of Supported Vesicular Layers on Titanium Dioxide by Quartz Crystal Microbalance With Dissipation Measurements*, The Journal of Chemical Physics 122 (2005) 8 pages.
Richter, R. et al., *Pathways of Lipid Vesicle Deposition on Solid Surfaces: A Combined QCM-D and AFM Study*, Biophysical Journal, vol. 85 (Nov. 2003) 3035-3047.

(56) References Cited

OTHER PUBLICATIONS

Richter, R. P. et al., *Following the Formation of Supported Lipid Bilayers on Mica; A Study Combining AFM, QCM-D, and Ellipsometry*, Biophysical Journal, vol. 88 (May 2005) 3422-3433.

Richter, R. P. et al., *Formation of Solid-Supported Lipid Bilayers: An Integrated View*, Langmuir 22 (2006) 3497-3505.

Rodahl, M. et al., *Simultaneous Frequency and Dissipation Factor QCM Measurements of Biomolecular Adsorption and Cell Adhesion*, Faraday Discuss., 107 (1997) 229-246.

Roskamp, R. F. et al., *Functional Tethered Bilayer Lipid Membranes On Aluminum Oxide*, ChemPhysChem 9 (2008) 1920-1924.

Sackmann, E., *Supported Membranes: Scientific and Practical Applications*, Sciences, vol. 271 (Jan. 1996) 43-48.

Schonherr, H. et al., *Vesicle Adsorption and Lipid Bilayer Formation on Glass Studied by Atomic Force Microscopy*, Langmuir 20 (2004) 11600-11606.

Tamm, L. K. et al., *Supported Phospholipid Bilayers*, Biophys. J., vol. 47 (Jan. 1985) 105-113.

Tayebi, L. et al., *Long-Range Interlayer Alignment of Intralayer Domains in Stacked Lipid Bilayers*, Nature Materials, vol. 11 (2012) 7 pages.

Tero, R. et al., *Lipid Bilayer Membrane With Atomic Step Structure: Supported Bilayer on a Step-and-Terrace $TiO_2(100)$ Surface*, Langmuir 24 (2008) 11567-11576.

Turvo, V. V. et al., *Application of H NMR Spectroscopy Method For Determination of Characteristics of Thin Layers of Water Adsorbed on the Surface of Dispersed and Porous Adsorbents*, Advances in Colloid and Interface Science 79 (1999) 173-211.

Venkatesan, B. M. et al., *Lipid Bilayer Coated $Al_2O_3$ Nanopore Sensors: Towards a Hybrid Biological Solid-State Nanopore*, Biomed Microdevices 13 (2011) 671-682.

Voinova, M. V. et al., *'Missing Mass' Effect in Biosensor's QCM Applications*, Biosensors and Bioelectronics 17 (2002) 835-841.

Von Tscharner, V. et al., *Physical Properties of Lipid Monolayers on Alkylated Planar Glass Surfaces*, Biophys. J., vol. 36 (Nov. 1981) 421-427.

Watts, T. H. et al., *Antigen Presentation by Supported Planar Membranes Containing Affinity-Purified $I-A^d$*, Proc. Natl. Acad. Sci., vol. 84 (Dec. 1984) 7564-7568.

Zhdanov, V. P. et al., *Comments on Rupture of Adsorbed Vesicles*, Langmuir 17 (2001) 3513-3521.

Zhdanov, V. P. et al., *Simulation of Adsorption Kinetics of Lipid Vesicles*, Journal of Chemical Physics, vol. 112, No. 2 (Jan. 2000) 900-909.

Internatioanl Search Report and Written Opinion for Application No. PCT/SG2014/000449 dated Oct. 22, 2014.

\* cited by examiner

METHODS FOR CONTROLLING ASSEMBLY OF LIPIDS ON A SOLID SUPPORT

FIELD OF THE INVENTION

The invention relates to methods of controlling adsorption of lipid molecules onto a solid support.

BACKGROUND OF THE INVENTION

Lipid bilayer membranes on solid supports are a widely studied model system to understand the structure and function of biological membranes. There are many applications of lipid bilayer membranes on solid supports, including but not limited to biosensors, biocompatible surface coatings, and targeted drug delivery systems. Self-assembly fabrication of lipid bilayer membranes taking advantage of liposome adsorption and spontaneous rupture on material substrates is popular, because the method does not require mechanical forces, occurs only at the solid-liquid interface, and is based on the diffusion-limited adsorption of liposomes onto the solid support. A wide range of experimental parameters influence the self-assembly process, including liposome properties (e.g., size, lipid composition, lamellarity and osmotic pressure), solution conditions (e.g., ionic strength, temperature, solution pH) and material properties (e.g., crystallinity, topology).

Traditionally, adjustment of electrostatic forces has been the primary aim of interfacial science approaches to tune lipid-substrate interactions but this approach is not always successful and the results are inconsistent. An example is the formation of a planar lipid bilayer on a solid support. On titanium oxide, formation of a planar bilayer by zwitterionic lipid vesicle adsorption and spontaneous rupture occurs at pH 4, which is below the isoelectric point (IEP) of titanium oxide (Tayebi, et al. Nature Materials 2012, Vol 11 pages 1074-1080). However, on aluminum oxide, formation of a planar bilayer by zwitterionic lipid vesicle adsorption and spontaneous rupture does not occur under the same pH condition, although the condition is also below the isoelectric point of aluminum oxide (Keller, et al. Biophysical Journal 1998, 75, (3), 1397-1402). Considering that, in both cases, there is electrostatic attraction between the negatively charged zwitterionic lipid vesicles and the positively charged substrates, the evidence supports that electrostatic attraction and methods to tune electrostatic forces are insufficient to form planar bilayers as a general means.

It is generally understood that the overall adhesion process depends on the material properties of the solid support. Liposomes typically adsorb and either remain intact (e.g., gold and titanium oxide) or rupture to form a planar bilayer (e.g., silicon oxide and mica). Groves et al. (Langmuir 1998, 14, (12), 3347-3350) have reported that several oxide film substrates may serve as barriers that prevent the self-assembly of lipid bilayer membranes, including aluminum oxide, which can hinder liposome adsorption. As some substrates may serve as barriers that prevent the self-assembly of lipid bilayer membranes, the range of solid supports that can be used to support lipid bilayers is quite narrow. Groves et al. identified Type I barriers such as aluminum oxide that can prevent vesicle adsorption, and Type II barriers such as indium tin oxide and chrome that support vesicle adsorption but the resulting bilayers are effectively immobile.

Several methods have been developed to form lipid bilayer membranes on solid supports which are intractable to liposome adsorption and spontaneous rupture, including covalently attaching auxiliary materials that facilitate adsorption and rupture of liposomes to the solid support. However, it has proven problematic to form a complete lipid bilayer membrane without adulterating the properties of the solid support or the lipid bilayer membrane through covalent modifications. These covalent modifications are time consuming, expensive and usually only work over small segments of the substrate.

Therefore, there is need in the art for strategies that overcome the limitations of existing support materials while circumventing the laborious and costly surface modification approach.

Furthermore, attempts to form lipid bilayer membranes on solid supports have only focused on the positive case, i.e., methods to form planar bilayers. There is also a need to develop methods to inhibit the formation of lipid bilayer membranes on solid supports tractable to vesicle adsorption and spontaneous rupture. As some materials adhere to cell membranes and lead to cell rupture, current nanoparticles and devices used in animals including humans are limited to a narrow range of materials that are not harmful to cells. This limitation makes the range of materials suitable for nanoparticles and devices for targeted drug delivery very narrow.

Accordingly, there is also need in the art for materials or methods that overcome the existing limitation in that the materials are imparted lipid rejecting properties.

SUMMARY OF THE INVENTION

In view of the above, it is an object of the invention to provide means to control adsorption of lipid molecules onto a solid support that are applicable to a wide range of solid supports.

The inventors have now surprisingly found that the adsorption of lipid molecules onto a solid support surface and the formation of lipid structures on said surface can be finely tuned by influencing the steric-hydration force of the lipids and the support surface.

In a first aspect, the invention therefore relates to a method of controlling adsorption of lipid vesicles onto a solid support comprising: tuning the steric-hydration force of the lipid vesicles and the surface of the solid support such that (i) the lipid vesicles rupture and form a bilayer membrane structure on the solid support; or (ii) the lipid vesicles are stably adsorbed to the solid support; or (iii) the adsorption of the lipid vesicles onto the solid support is inhibited.

Another aspect of the invention relates to a solid support comprising a stabilized lipid bilayer adsorbed thereon obtainable according to the methods described herein.

Another aspect of the invention relates to a solid support resisting lipid vesicle adsorption thereon obtainable according to the methods described herein.

Other aspects of the invention will be apparent to a person skilled in the art with reference to the following drawings and description of various non-limiting embodiments.

BRIEF DESCRIPTION OF THE FIGURES

The drawings are not necessarily drawn to scale, emphasis instead generally being placed upon illustrating the principles of various embodiments. In the following description, various embodiments of the invention are described with reference to the following drawings.

DETAILED DESCRIPTION OF THE INVENTION

Figure 1:
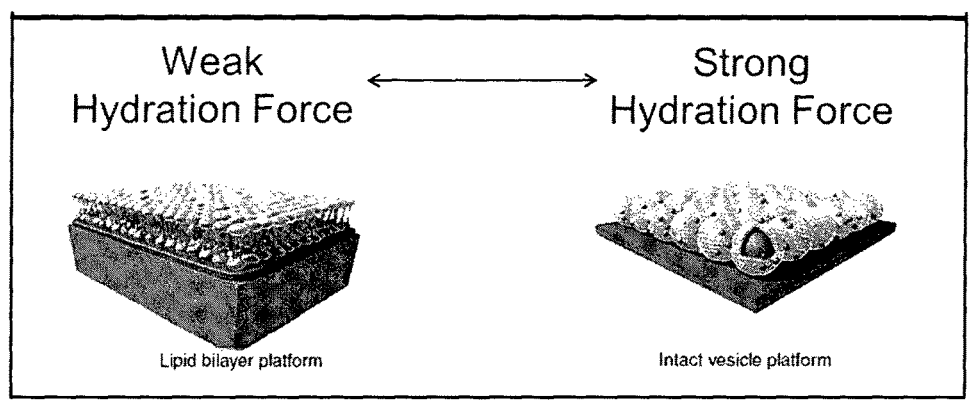
FIG. 1. Conditions to control the interaction of lipid assemblies with solid supports. Conditions that induce weak steric-hydration force (weakly destabilizing) promote the formation of a two-dimensional, planar lipid bilayer. Conditions that induce strong steric-hydration force (strongly destabilizing) promote the formation of an intact vesicle layer because the total interaction energy is not strong enough to promote vesicle rupture.

A method to control the interaction between lipid assemblies and inorganic materials was developed, which is based on an integrated framework to analyze the interaction of lipid assemblies on solid supports through three contributing interfacial forces, specifically the van der Waals force, double-layer electrostatic force and steric-hydration force. The van der Waals force is an attractive force between the planar lipid bilayer and the oxide film substrate. Hence, it always contributes positively to stabilization of solid-supported lipid assemblies. By contrast, the electrostatic double-layer interaction energy can be either repulsive or attractive, and hence its contribution to the total interaction energy is variable. The steric-hydration force is always repulsive, but the magnitude of the force varies and this is a key contributor to balance the other two forces to provide thermodynamic stabilization for the system.

Taken together, this framework provides a model which has three key contributions. First, it validates empirical findings that attractive electrostatic forces are important but not essential or sufficient for promoting vesicle rupture on solid supports. Second, it demonstrates that the steric-hydration force is also important to control the interaction of lipid assemblies with solid supports. Third, it demonstrates for the first time that the balance of these forces is the main contributor, primarily governed by the steric-hydration force, to dictate how lipid assemblies interact with solid supports. Electrostatic forces, attractive, repulsive, or negligible depending on design scheme, are insufficient without requisite steric-hydration force conditions to control lipid adsorption. This knowledge provides design principles that can promote or inhibit the formation of planar bilayers and/or vesicle adsorption on a wide range of different solid supports.

Accordingly a first aspect of the invention relates to a method of controlling adsorption of lipid vesicles onto a solid support comprising: tuning the steric-hydration force of the lipid vesicles and the surface of the solid support such that (i) the lipid vesicles rupture and form a bilayer membrane structure on the solid support; or (ii) the lipid vesicles are stably adsorbed to the solid support; or (iii) the adsorption of the lipid vesicles onto the solid support is inhibited.

The term "steric-hydration force", as used in this connection, is a strong short range, typically repulsive, force between polar surfaces separated by a thin layer (<3 nm) of water and/or ions and decays quasi-exponentially with the surfaces' spacing. It can be characterized by the decay length λ. The steric-hydration force may be tuned between a decay length of 0.1 and 0.6 nm by adjusting the spatial density and size of functional groups on the surface of the solid support. A weak steric-hydration force has a weakened magnitude of repulsion having less repulsion and is characterized by a shorter decay length towards 0.1 nm. A strong steric-hydration force has a strengthened magnitude of repulsion having greater repulsion and is characterized by a larger decay length towards 0.6 nm. The steric-hydration force is independent of the IEP.

In various embodiments, the method further comprises tuning the electrostatic forces between the surface of the lipid vesicles and the surface of the solid support. In various embodiments, both the electrostatic force, which is preferably attractive, and the steric-hydration force, which is typically repulsive, are finely tuned such that the desired form of lipid adsorption, including resisting the lipid adsorption, is achieved.

The term "electrostatic force", as used in this connection, refers to a force between electrical charges, for example on the surface of objects, which can be attractive in case of opposite charges or repulsive in case of the same charges. Preferably, the solid support surfaces used in connection with the methods described herein have a positive charge, while the lipid vesicles are preferably negatively charged. This results in the electrostatic force between lipid vesicles and the solid support surface being attractive.

Conditions that induce attractive electrostatic force (strongly stabilizing) and weak steric-hydration force (weakly destabilizing) promote the formation of a two-dimensional, planar lipid bilayer. Conditions that induce repulsive electrostatic forces (strongly destabilizing) and strong steric-hydration force (strongly destabilizing) promote the formation of an intact vesicle layer (or complete inhibition of vesicle adsorption) because the total interaction energy is not strong enough to promote vesicle rupture (or vesicle adsorption).

The inventors have found that the magnitude and direction of the electrostatic force can be controlled by the solution pH and the ionic strength. The magnitude and direction of this force depend on the solution pH relative to the isoelectric point (IEP), the isoelectric point being an intrinsic material property corresponding to the pH value at which the surface has a net charge of about zero. Solution pH values below the IEP lead to positive net surface charges, and solution pH values above the IEP lead to negative net surface charges. Ionic strength controls the magnitude of the force insofar as that greater ionic strength attenuates the surface charge. Adjusting these conditions is useful for optimizing control over lipid adsorption onto solid supports.

In various embodiments the steric-hydration force of the solid support is tuned by controlling the pH. This adjustment influences the protonation state of functional groups on the surface and may influence bonding patterns between functional groups and between functional groups and water molecules. The pH control does not adjust the density of functional groups on the surface. Similarly, if desired, also the electrostatic forces may, in cases, be tuned by pH control depending on the IEP and the properties of the material. The pH control is typically done by changing the pH of the solution in which the lipid vesicles are provided and which is brought into contact with the solid support surface. The pH change can be done by any means known in the art and specifically includes the addition of an acid or a base. The pH change can be monitored by known means, for example by means of a pH measuring electrode. The desired pH can for example be achieved by titrating the solution with an acid (for pH decrease) or a base (for pH increase) while monitoring the change via a pH electrode. In various embodiments, the tuning of the steric-hydration force and, optionally, the electrostatic forces is achieved by setting the pH to about 1.5 to 4.5, preferably pH 2 to 3.

In various other embodiments that can be used in alternative to the pH change described above but also in combination therewith, the steric-hydration force and, optionally, also the electrostatic force of the solid support are tuned by pretreating the surface of the solid support. The pretreatment changes the properties of the surface with respect to the hydration properties. Typically, this change is caused by modification of surface exposed functional groups of the support material either by chemical (such as by reaction with another agent) or by physical (such as irradiation, heating, etc.) means. In some cases, pretreatment may change the protonation state of functional groups on the surface and may influence bonding patterns between functional groups and between functional groups and water molecules. Negatively charged functional groups may cause dipole alignment of water molecules leading to a strong repulsive steric-hydration force. Uncharged functional groups may cause hydrogen-bonded water molecules leading to a weak repulsive steric-hydration force. In other cases, pretreatment may change the spatial density of functional groups on the surface and affect the formation of hydration layers on the surface.

In various embodiments, the pretreatment of the support surface may include techniques such as, without limitation, thermal annealing, chemical titration, exposure to oxygen plasma, chemically modifying functional groups, treatment with a reducing or oxidizing agent, treatment with a catalyst, exposure to ultraviolet light, or the non-covalent attachment of ions to the solid support. The protonation state of the functional group, the spatial density of the functional group, and ions attached to the functional group are some of the factors involved in mediating the magnitude of the steric-hydration force.

As mentioned above, generally a solid support already has functional groups on its surface and modifying these functional groups by any of the pretreatments mentioned herein can affect the steric-hydration force which in turn affects the interaction between the lipid vesicles and/or the surface of the solid support.

The type of functional groups that are present on the support surface depend on the material of the support and typically include, without being limited thereto, any one or more of hydroxyl (—OH), carboxyl (—COOH), carbonyl (—C(=O)—, amine (—NR$_2$), sulfhydryl (—SH) or phosphate (—PO$_4^{2-}$) groups.

In various embodiments the pretreatment has the effect of reducing the spatial density of the functional groups on the surface. Such pretreatments may include exposure to oxygen plasma or exposure to ultraviolet light that may reduce the number of functional groups on the surface. Heat treatment such as thermal annealing may cause dissociation of the surface functional groups. Similarly chemical titration may actually remove surface functional groups.

Without wishing to be limited to any particular theory, it is however assumed that the surface functional groups create an energy barrier related to the repulsive steric-hydration force and reducing the spatial density of functional groups on the surface effectively decreases the strength of the repulsive steric-hydration force permitting the formation of a lipid bilayer on the solid support.

In various embodiments the pretreatment comprises protonating or deprotonating functional groups on the surface of the solid support. Where the pretreatment comprises protonating the surface functional groups a hydrogen bonding network is formed. The surface functional groups may be protonated by reducing agents or catalysts.

In various non-limiting embodiments, the ions non-covalently attached to the solid support surface are selected from the group consisting of magnesium, calcium and strontium.

Such ions may be non-covalently attached to the surface of the substrate by incubating the surface with an aqueous solution of the respective metal salts such as calcium chloride that will result in attachment of the calcium ions to the functional groups on the surface of the solid support.

Without wishing to be limited to any particular theory, it is however assumed that this increases the decay length of the steric-hydration force preventing lipid vesicle absorption on the solid support.

In various embodiments the solid support comprises or consists of a material that is selected from metalloids, metalloid oxides, metals, metal oxides, and semiconductors. Alternatively, the solid support may have a surface or surface layer consisting of any one of these materials.

Metalloid oxides, as used herein, include silicon oxides and materials containing them, such as glass, silica and quartz.

Suitable metals for the solid support include, without limitation titanium, aluminum, and gold.

Metal oxides that can be used include, without limitation, aluminum oxide (alumina) and titanium oxide (titania).

Semiconducting materials that may be used for the solid support include, without limitation, silicon and indium tin oxide.

In preferred embodiments, the solid support material is a metal oxide, preferably aluminum oxide or titanium oxide.

In principle, the solid support may have any form or structure. It is however preferred that it includes a planar structure. Accordingly, the solid support may have the form of a plate or disk.

In various other embodiments the solid support comprises or consists of a particle, in particular a micro- or nanoparticle, preferably a nanoparticle. The nanoparticles may have a size between 2-400 nm, or 40-100 nm in diameter and are typically essentially spherical.

The nanoparticle may be suitable for use in an animal body such as a human body. In various embodiments the nanoparticle is suitable for drug delivery to an animal body.

In various embodiments the lipid vesicles are provided in form of an emulsion in an aqueous solvent. It is to be understood that while throughout the present disclosure reference is made to lipid vesicles that the invention is not limited to such vesicles, but that other lipid assemblies can similarly be used. For example, other ordered lipid structures, like lamellar, cubic or tubular structures, or lipid aggregates may be equally suitable. It is thus understood that when reference is made herein to "lipid vesicles", this is by way of illustration and not limitation and that the term may include lipid assemblies in general.

In various embodiments the lipid vesicles are liposomes. The liposomes are preferably artificially prepared spherical vesicles composed of lipids. The liposomes may have a mean diameter in the range of 10-100 nm, preferably 50-80 nm or more preferably 60-70 nm. Preferably, the liposomes are unilamillar with a single lipid bilayer.

The lipids forming the lipid vesicles, in particular the liposomes, may be selected from any suitable lipids and include well-known lipids, such as, for example, phospholipids, in particular glycerophospholipids, such as phosphatidylcholine, phosphatidylethanolamine, phosphatidic acid, phosphatidylinositol and/or phosphatidylserine, or sphingolipids. While these are preferred lipids, any other lipid known to be suitable to form lipid vesicles/liposomes may similarly be used either individually or in combination, for example in combination with the aforementioned phospholipids.

Examples for other lipids or lipid-like compounds that may be used include, without limitation, trigylcerides, waxes, isoprenoids, in particular steroids, such as cholesterol, fatty acids, fatty alcohols and lipopolysaccharides.

The lipids are typically characterized in that they comprise a polar or electrically charged, preferably (at neutral pH, i.e. about pH=7) negatively charged head group and an unpolar, uncharged tail group, the latter typically being a hydrocarbon, such as alkyl or alkenyl group.

The lipids used may be natural or synthetic in origin. While naturally occurring lipids, either isolated from natural sources or synthetically prepared, are preferred, it is also possible to use artificial lipids, for example lipids that have been modified compared to their natural counterparts.

In various embodiments, the lipid vesicles further comprise non-lipid components, such as proteins or peptides. Proteins or peptides that are to be used are preferably membrane-bound or membrane-associated proteins. Accordingly, the proteins and/or peptides may comprise lipid-like modifications, such as isoprenoid modifications, typically farnesyl or geranylgeranyl anchors, membrane-spanning domains or structures, or other domains or structures that facilitate membrane interaction by hydrophobic interactions.

In various embodiments the steric-hydration force and, optionally, the electrostatic force of the solid support are tuned by pretreating the solid support to reduce the magnitude of the repulsive steric-hydration force and, optionally, promote electrostatic attraction, preferably both. This provides a support surface that promotes lipid vesicle adhesion and subsequent rupture, such that the lipid vesicles form a stabilized bilayer membrane structure on the solid support. Generally, the formation of such a bilayer structure may include some deformation of the vesicles upon adsorption that leads to fusing of the vesicles and subsequent self-assembly of a lamellar bilayer structure on the support surface.

Figure 2:
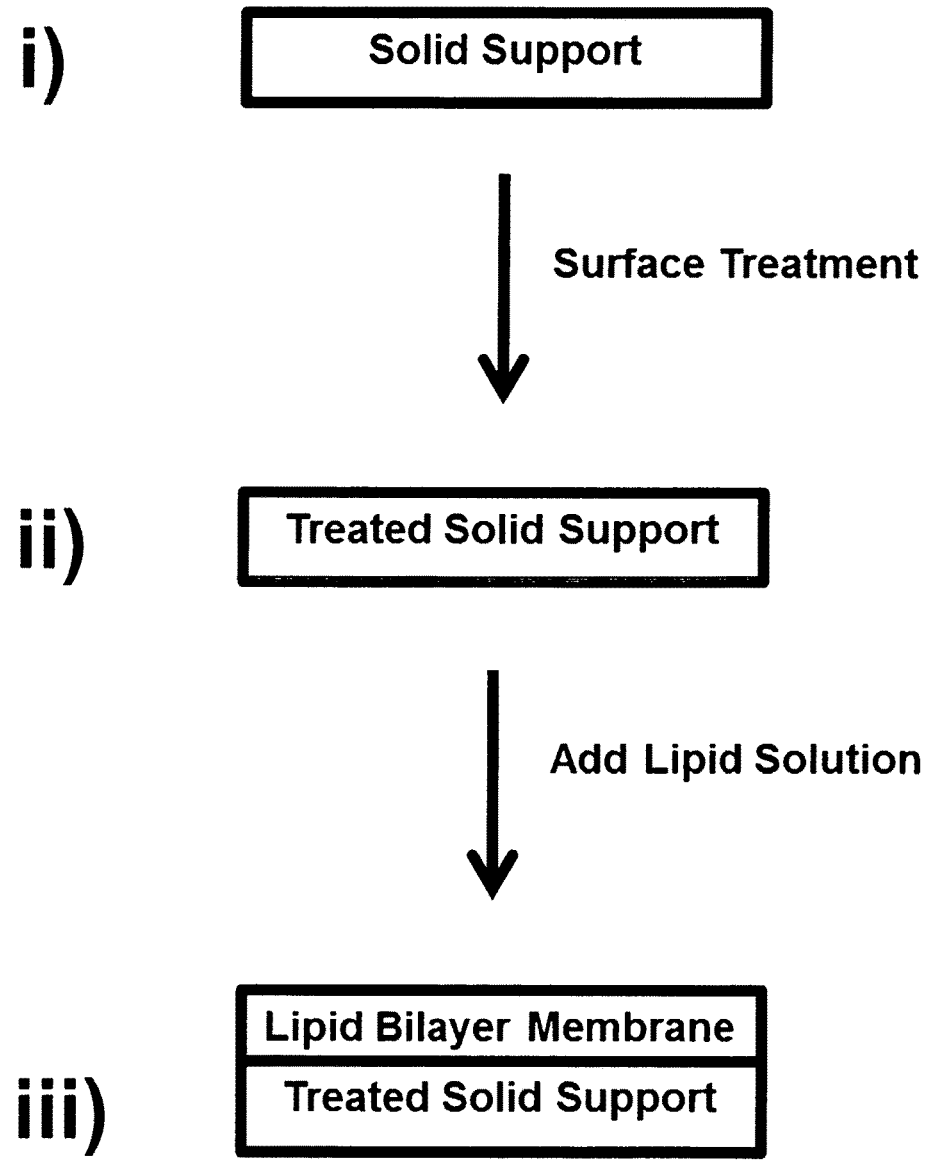
FIG. 2 schematically shows a method to A) stabilize a lipid bilayer membrane on a solid support and B) inhibit formation of a lipid bilayer membrane on a solid support.
Figure 2:
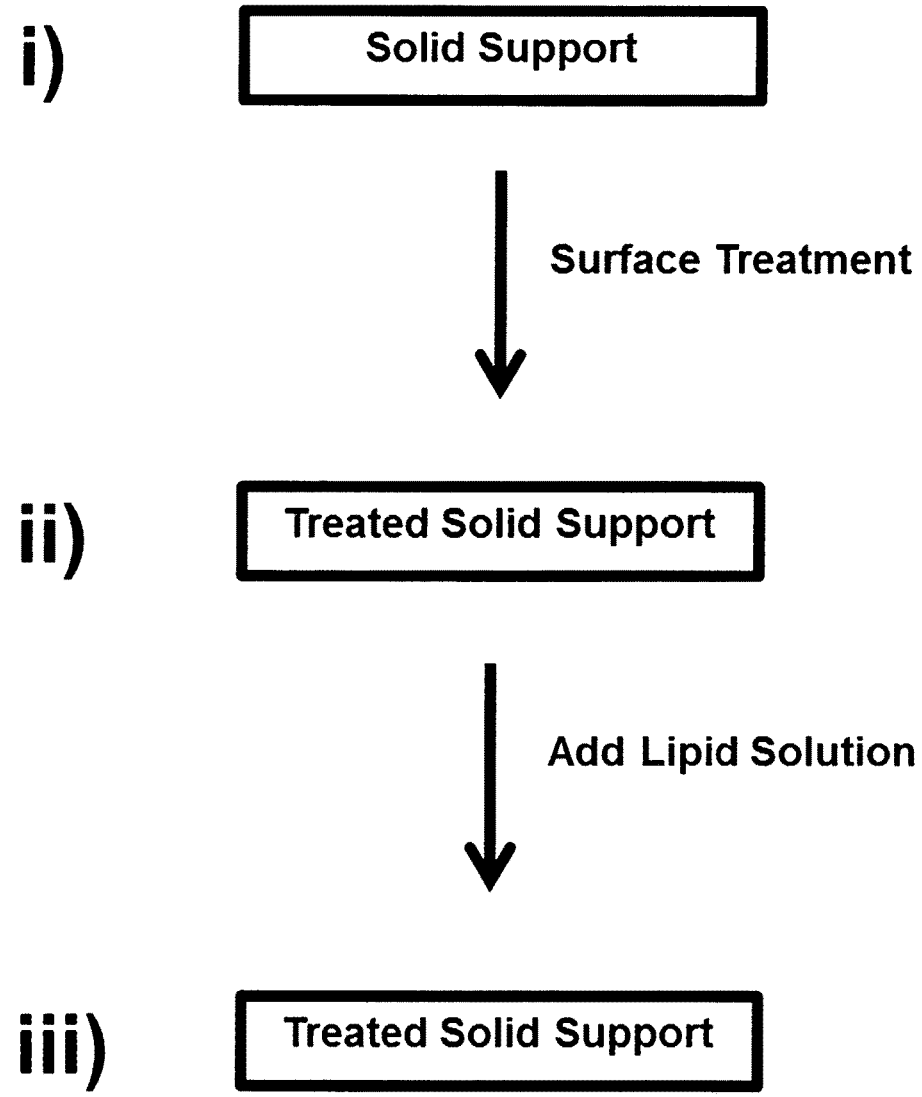

To achieve such an bilayer formation-promoting support surface, which is also referred herein as a surface which stabilizes bilayer membrane structures, the pretreatment may be selected from the group consisting of thermal annealing, chemical titration, exposure to oxygen plasma, exposure to ultraviolet light, protonating functional groups on the surface of the solid support, treatment with a reducing agent, or treatment with a catalyst. The pretreatment is believed to have the effect of stabilizing the formation of a lipid bilayer on the solid support (FIG. 2A).

In various embodiments, the presently described methods aim at providing surfaces that resist bilayer formation or lipid vesicle adsorption in general. In these cases, it is desirable that the steric-hydration force and, optionally, the electrostatic force of the solid support are tuned by pretreating pretreatment the solid support in order to increase the magnitude of the steric-hydration force and, optionally, increase electrostatic repulsion such that adsorption of the lipid vesicles onto the solid support is inhibited.

The treatment necessary to achieve such effect may aim at increasing the repulsive steric-hydration force that blocks interaction between the lipids/lipid vesicles and the surface of the solid support.

To achieve this, the pretreatment may be selected from the group consisting of chemical titration, exposure to oxygen plasma, exposure to ultraviolet light, deprotonating functional groups on the surface of the solid support, chemical titration, an oxidizing agent, or treatment with a catalyst. The pretreatment aims at increasing the spatial density of the functional groups and/or inducing ionization of the functional groups, and thus increasing the magnitude of the steric-hydration force, which in turn inhibits formation of a lipid bilayer on the solid support (FIG. 2B).

In various embodiments of the invention, the control of lipid vesicle adsorption is done by control of the solution pH. Such pH control may be used for the pretreatment of the solid support but may also be used to directly tune the interaction between lipid vesicles and solid support. Where the solid support is an oxide film with hydroxyl functional groups, the steric-hydration force is weakened by decreasing the pH to a range of about pH 2-3, as at this pH the hydroxyl groups of the oxide induce the formation of a hydration layer that embodies a weaker steric-hydration force. This enables the formation of a lipid bilayer on the solid support. In contrast known methods only call for decreasing the pH slightly below the isoelectric point of the support material. This typically leads to protonation of the support surface, thus increasing its positive charge, which in turn results in increased electrostatic attraction forces. However, it has been found that these methods lead only on some substrates to the formation of a lipid bilayer on the solid support. Surprisingly, the inventors have now found that even the previously unsuited solid support materials can accommodate lipid bilayer formation, if the pH is not only lowered slightly below the IEP, but rather to a value where the steric-hydration force can be tuned. This range is typically between about pH 2 and 3 for oxide films with hydroxyl functional groups.

The present invention also encompasses the structures obtainable by the methods described herein. In various embodiments, these structures are the solid supports comprising a stabilized lipid bilayer adsorbed thereon that are obtainable according to the methods described above. In other embodiments, the structures are the solid supports resisting lipid bilayer formation and/or lipid vesicle adsorption thereon that are obtainable according to the methods described above.

As described above the present invention focuses on the formation thermodynamics of model membranes on solid surfaces, such as oxide substrates, to either promote or prevent the formation of the planar lipid bilayers. The insight gained from the experiments allowed the formation of a lipid bilayer on aluminum oxide, which was previously not considered possible due to the properties of aluminum oxide surfaces.

In addition, the finding that surfaces that were previously assumed to strongly promote lipid adsorption and bilayer formation can be treated such that they become resistant to lipid adsorption and bilayer formation, advantageously lead to a possibility for the reduction of cytotoxicity of nanoparticles, such as those intended for therapeutic uses. This reduced cytotoxicity can be attributed to the fact that the nanoparticles resist adsorption to lipids, as they occur in the cell membranes.

Generally, the terms used herein have, unless explicitly stated otherwise, the accepted meaning in the art.

By "comprising", as used herein, it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

The following examples are illustrative of the invention and its preferred embodiments, and are not to be taken as limiting the disclosure or claims in any way.

EXAMPLES

Example 1: Formation of a Lipid Bilayer Membrane on Aluminum Oxide

Surface Treatment.

For all experiments, AT-cut crystals (Q-Sense) with 14 mm diameter and a 50 nm thermally evaporated aluminum oxide coating were used. Prior to experiment, each sensor crystal was treated with oxygen plasma at 80 W for 5 min (March Plasmod Plasma Etcher, March Instruments, California).

Vesicle Preparation.

Small unilamellar vesicles composed of 1-palmitoyl-2-oleoyl-sn-glycero-3-phosphocholine (POPC) (Avanti Polar Lipids, Alabama, USA) were prepared according to the extrusion method, as previously described. Extrusion was performed through a series of track-etched polycarbonate membranes with decreasing 100, 50 and 30 nm pore sizes. Vesicles were prepared using a Tris buffer solution (10 mM Tris and 150 mM NaCl, pH 7.4) at a nominal lipid concentration of 5 mg·mL$^{-1}$. Before the experiment, the resulting small unilamellar vesicles were diluted in the appropriate Tris buffer solution to 0.125 mg·mL$^{-1}$ concentration, and were used within 24 hours of preparation. All buffer solutions were prepared in 18.2 MΩ·cm MilliQ water (MilliPore, Billerica, Mass.). The average diameter of the vesicles was 60-nm, as measured by dynamic light scattering Dynamic Light Scattering.

The size distribution of extruded vesicles was determined by using a 90Plus particle size analyzer (Brookhaven Instruments, Holtsville, N.Y., USA) that was equipped with a 658.0 nm monochromatic laser. In order to minimize the reflection effect, the scattering angle was set at 90°. Experimental data was collected by digital autocorrelator software, and all autocorrelation functions were analyzed by CONTIN and nonnegatively constrained least-squares algorithms to identify multimodal distributions, if any. For experiments reported in this work, the average diameter of vesicles was 60.3 nm with a polydispersity of 0.054, which is in agreement with literature values Quartz Crystal Microbalance-Dissipation (QCM-D) Method.

The adsorption kinetics of POPC lipid vesicles onto aluminum oxide were monitored by a Q-Sense E4 (Q-Sense AB, Gothenburg, Sweden), as previously described (Richter & Brisson, 2005 Biophysical Journal 88 (5), 3422-3433). For all experiments, AT-cut crystals (Q-Sense) with 14 mm diameter and a 50 nm thermally evaporated aluminum oxide coating were used. Prior to experiment, each sensor crystal was treated with oxygen plasma at 80 W for 5 min (March Plasmod Plasma Etcher, March Instruments, California). Experimental data was recorded at the third (15 MHz), fifth (25 MHz) and seventh (35 MHz) overtones, and the data presented in the main text was recorded at the third overtone (15 MHz). The temperature of the measurement cell was 25.0° C. with fluctuations no greater than ±0.5° C.

Controlling Formation of Lipid Bilayers.

Figure 3:
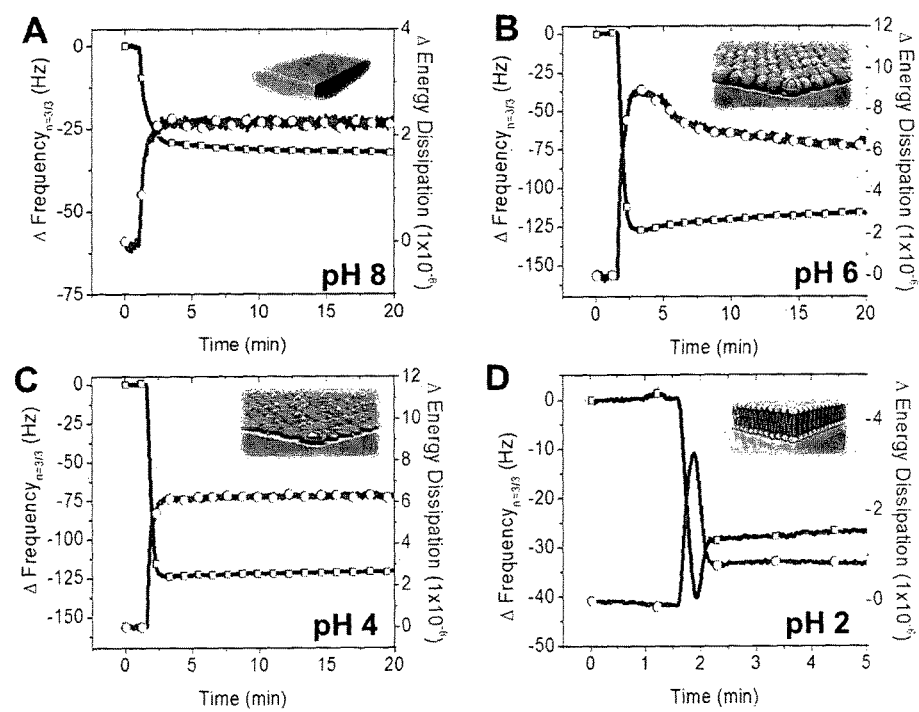
FIG. 3. QCM-D monitoring of pH-dependent vesicle adsorption onto aluminum oxide. Graphs depict resonance frequency (Δf) and energy dissipation (ΔD) shifts as function of time as black and grey curves, respectively. (A) at pH 8, there was minimal vesicle adsorption. (B) at pH 6, vesicles adsorbed reversibly. (C) at pH 4, vesicles adsorbed irreversibly. (D) at pH 2, a planar lipid bilayer was formed.

Chemical titration strategies were employed in order to control adsorption kinetics of POPC lipid vesicles onto an aluminum oxide surface, as monitored by using the quartz crystal microbalance with dissipation (QCM-D) monitoring technique (FIG. 3). Before experiment, surfaces were incubated in solutions of varying pH in order to change the protonation state of hydroxyl functional groups on the aluminum oxide surface.

The average diameter of the vesicles was 60-nm. After establishing a baseline signal, vesicles were added and changes in resonance frequency ($\Delta f$) and energy dissipation ($\Delta D$) were monitored as functions of time. At pH 8, vesicle addition led to changes in resonance frequency and energy dissipation of −32 Hz and 2.2×10$^{-6}$, respectively (FIG. 3A). The $\Delta D/\Delta f$ ratio is indicative of a viscoelastic adsorbate, suggesting the adsorption of a few vesicles rather than a planar bilayer. The same experiment was also performed at pH 8.5, no vesicle adsorption was observed. This treatment prevents vesicle adsorption on the aluminum oxide support.

At pH 6, vesicle addition led to the formation of an intact vesicle adlayer (=adsorbed layer) (FIG. 3B). The maximum changes in resonance frequency and energy dissipation were −126 Hz and $8.7 \times 10^{-6}$, respectively, which are consistent with an intact vesicle adlayer. However, there was a change in the physical properties of the adlayer as flow continued. Within 15 min, the final changes in resonance frequency and energy dissipation had reached −116 Hz and $6.3 \times 10^{-6}$, respectively. Reversible vesicle adsorption suggests relatively weak vesicle-substrate interactions. At pH 4, vesicle addition led to changes in resonance frequency and energy dissipation of only −121 Hz and $6.3 \times 10^{-6}$, respectively (FIG. 3C). The vesicle adlayer was irreversibly adsorbed, suggesting stronger vesicle-substrate interaction as compared to pH 6.

Vesicle adsorption was next investigated at pH 2 (FIG. 3D). Two-step adsorption kinetics were observed, which corresponded to planar bilayer formation via vesicle rupture after reaching a critical coverage. Upon adsorption, the critical vesicle coverage corresponded to changes in resonance frequency and energy dissipation of −40 Hz and $3.0 \times 10^{-6}$, respectively. Afterwards, vesicles began to rupture and the final changes in resonance frequency and energy dissipation were −24 Hz and $0.6 \times 10^{-6}$, respectively. Taken together, the QCM-D measurement results indicate that chemical titration influences the interaction between vesicles and aluminum oxide.

Equation Validation Data

Experimental data for controlling lipid adsorption onto silicon oxide and aluminum oxide as representative materials. Mathematical equations describe how to control the interaction via modulating the steric-hydration force on titanium oxide as a representative material. A general equation is described below:

$W_1$=van der Waals force $W_2$=Double-layer electrostatic force $W_3$=Steric-hydration Force $W_{Total}$=Total Interaction Energy $W_0$=Threshold Energy $W_{Total} = W_1 + W_2 + W_3$ The methods described herein may control $W_{Total}$ to be greater or less than $W_0$ in order to promote attractive or repulsive interactions between lipid membranes and oxide materials. $W_1$ and $W_2$ are fixed parameters under physiological conditions and $W_3$ may be freely tuned within a certain range (decay length, $\lambda_0$, between 0.1 and 0.6 nm).

The isoelectric point of aluminum oxide is reported to be approximately 8.8. Below this pH, the substrate has a positive charge while the vesicles are negatively charged. Nevertheless, the vesicles only weakly adsorb and do not form a planar bilayer until pH 2. Changes in the double-layer electrostatic force are insufficient to explain the experimental findings on aluminum oxide. It is likely that the steric-hydration force is the primary factor controlling adsorption of lipid vesicles onto aluminum oxide, and hence this finding enables additional strategies to adjust the steric-hydration force.

Since the electrostatic force is not the main factor, the pH effect is likely due to either the van der Weals force or steric-hydration force. The van der Waals force is always attractive and its strength is independent of pH so the steric-hydration force is likely the main factor to explain the pH effect on aluminum oxide.

Vesicles interact with aluminum oxide, going from strong steric hydration force to a weak steric-hydration force in the following self-assembly pathway: (i) barrier; (ii) reversibly adsorbed vesicle adlayer; (iii) irreversibly adsorbed vesicle layer; and (iv) planar bilayer.

Example 2: Lipid Membrane Platforms on Silicon Oxide

Figure 4:
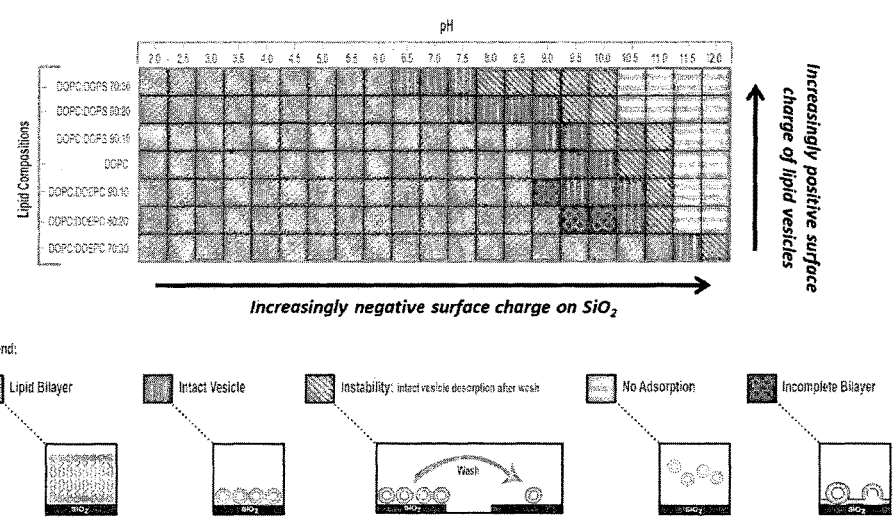
FIG. 4. Morphology Diagram of Model Membrane Platforms on Silicon Oxide. It is generally known in the art that lipid vesicles adsorb and rupture to form a planar bilayer on silicon oxide. However, the interaction between lipid vesicles and silicon oxide may be controlled. Using the prescribed methods to either promote or hinder this interaction, self-assembly of one of many different types of model membranes can occur on silicon oxide. Since the isoelectric point of silicon oxide is ~2, the observed behavior demonstrates that the double-layer electrostatic force is insufficient by itself to control the interaction between vesicles and the substrate. Specifically, bilayer formation may occur in the presence of electrostatic repulsion. Rather, the steric-hydration force can modulate this interaction, and strong steric-hydration force can inhibit bilayer formation even in cases of electrostatic attraction using, e.g., positively charged lipid vesicles. In turn, controlling the steric-hydration force interaction can be mediated by the prescribed method which tunes the steric-hydration force to be within an acceptable range.

Using the methods as described in Example 1 to either promote or hinder lipid self-assembly of many different type of model membranes on silicon oxide—a prototypical surface known in the art to promote bilayer formation under standard conditions—a scale was formed. Since the isoelectric point of silicon oxide is ~2, the observed behavior demonstrates that the double-layer electrostatic force is insufficient by itself to control the interaction between vesicles and the substrate (FIG. 4). In every case the pH that forms a lipid bilayer on the solid support is above the IEP. Rather, the steric-hydration force can modulate this interaction. In turn, controlling this interaction can be mediated by the prescribed method which tunes the steric-hydration force to be within an acceptable range.

Example 3: Resistance of Treated Titanium Oxide to Liposome Adsorption

Surface Treatment.

For all experiments, AT-cut crystals (Q-Sense) with 14 mm diameter and a 50 nm thermally evaporated titanium oxide coating were used. Prior to experiment, each sensor crystal was treated with oxygen plasma at 80 W for 5 min (March Plasmod Plasma Etcher, March Instruments, California).

Vesicle Preparation.

Small unilamellar vesicles composed of 70 mol % 1-palmitoyl-2-oleoyl-sn-glycero-3-phosphocholine (POPC) and 30 mol % 1-palmitoyl-2-oleoyl-sn-glycero-3-phospho-L-serine (sodium salt) (POPS) (Avanti Polar Lipids, Alabama, USA) were prepared according to the extrusion method, as previously described. Extrusion was performed through a series of track-etched polycarbonate membranes with decreasing 100, 50 and 30 nm pore sizes. Vesicles were prepared using a Tris buffer solution (10 mM Tris and 150 mM NaCl, pH 7.4) at a nominal lipid concentration of 5 mg·mL$^{-1}$. Before experiment, the resulting small unilamellar vesicles were diluted in the appropriate Tris buffer solution to 0.125 mg·mL$^{-1}$ concentration, and were used within 24 hours of preparation. All buffer solutions were prepared in 18.2 MΩ·cm MilliQ water (MilliPore, Billerica, Mass.).

QCM-D Method.

The adsorption kinetics of POPC lipid vesicles onto titanium oxide were monitored by a Q-Sense E4 (Q-Sense AB, Gothenburg, Sweden), as previously described above. For all experiments, AT-cut crystals (Q-Sense) with 14 mm diameter and a 50 nm thermally evaporated titanium oxide coating were used. Prior to experiment, each sensor crystal was treated with oxygen plasma at 80 W for 5 min (March Plasmod Plasma Etcher, March Instruments, California). Experimental data was recorded at the third (15 MHz), fifth (25 MHz) and seventh (35 MHz) overtones, and the data was recorded at the third overtone (15 MHz). The temperature of the measurement cell was 25.0° C. with fluctuations no greater than ±0.5° C.

Controlling Lipid Bilayers.

Figure 5:
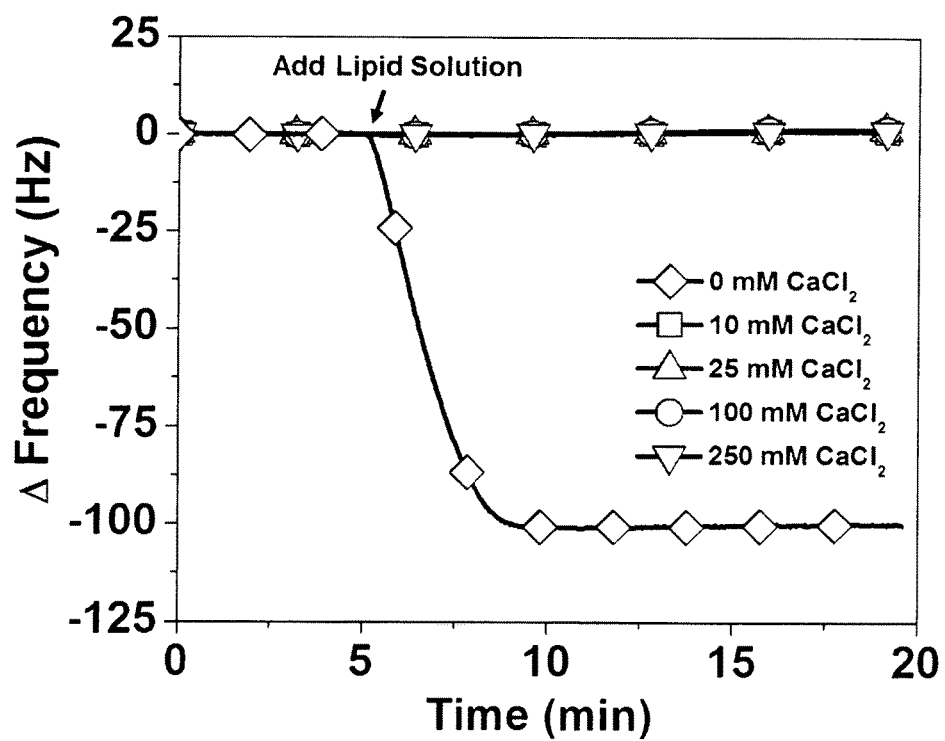
FIG. 5. QCM-D monitoring of vesicle adsorption onto titanium oxide pretreated with calcium ions. The graph depicts the resonance frequency (Δf) shift as a function of time. Before the measurement, the titanium oxide substrate was pretreated by incubation at room temperature in an aqueous buffer solution of $CaCl_2$ of the following molar concentration: 0, 10, 25, 100 or 250 mM, followed by rinsing with calcium-free aqueous solution.

Titanium oxide surfaces were pre-incubated with calcium chloride solutions in order to deposit divalent calcium ions on the substrate. Depending on the molar concentration of calcium chloride in solution, the layer coating could be adjusted in order to impart a steric-hydration force. After the incubation step, 70/30 mol % POPC/POPS lipid vesicles were added to the substrate and the vesicle adsorption process was tracked by QCM-D monitoring as shown in FIG. 5. The calcium layer imparts a positive charge so it was initially hypothesized that the attached calcium ions would facilitate rupture of the negatively charged vesicles.

To test this hypothesis, we first performed a control experiment in which the vesicles were added to a titanium oxide substrate that was not treated with calcium chloride before experiment. The average diameter of the vesicles was 70-nm. In this case, vesicle adsorption led to formation of an adsorbed vesicle layer with a final frequency shift of −104 Hz. By contrast, there was no frequency shift associated with vesicle adsorption to surfaces already containing attached calcium ions from deposited solutions of 10, 25, 100, or 250 mM calcium chloride despite an attractive electrostatic interaction. This indicates that attached calcium ions inhibit vesicle adsorption.

The invention claimed is:

1. A method of controlling adsorption of lipid vesicles onto a solid support comprising: tuning the steric-hydration force of the lipid vesicles and the surface of the solid support, and further tuning the electrostatic force between the surface of the lipid vesicles and the surface of the solid support, such that
   (i) the lipid vesicles rupture and form a bilayer membrane structure on the solid support; or
   (ii) the lipid vesicles are stably adsorbed to the solid support; or
   (iii) the adsorption of the lipid vesicles onto the solid support is inhibited.

2. The method according to claim 1, wherein the steric-hydration force and, optionally, the electrostatic force of the solid support are tuned by controlling the pH or pretreating the surface of the solid support.

3. The method according to claim 2, wherein the pretreatment comprises thermal annealing, chemical titration, exposure to oxygen plasma, chemically modifying functional groups, treatment with a reducing or oxidizing agent, treatment with a catalyst, exposure to ultraviolet light, or the non-covalent attachment of ions to the solid support.

4. The method according to claim 3, wherein the pretreatment comprises protonating or deprotonating functional groups on the surface of the solid support, preferably wherein the functional groups that are chemically modified comprise hydroxyl, carboxyl, carbonyl, amine, sulfhydryl, or phosphate groups.

5. The method according to claim 3, wherein the ions non-covalently attached to the solid support surface are selected from the group consisting of magnesium, calcium, and strontium.

6. The method according to claim 1, wherein the solid support comprises or consists of a metalloid or oxide thereof, a metal, a metal oxide, or a semiconductor.

7. The method according to claim 6, wherein the metal oxide is selected from the group consisting of aluminum oxide and titanium oxide.

8. The method according to claim 6, wherein the metalloid oxide is selected from the group consisting of glass, silica, and quartz.

9. The method according to claim 6, wherein the metal is selected from the group consisting of titanium, aluminum, and gold.

10. The method according to claim 6, wherein the semiconductor is silicon or indium tin oxide.

11. The method according to claim 1, wherein the solid support comprises a planar structure or a nanoparticle.

12. The method according to claim 1, wherein the lipid vesicles are liposomes.

13. The method according to claim 1, wherein the lipid vesicles are provided in form of an emulsion in an aqueous solvent.

14. The method according to claim 1, wherein the lipid vesicles comprise or are composed of phospholipids.

15. The method according to claim 1, wherein the lipid vesicles further comprise proteins or peptides.

16. The method according to claim 1, wherein the steric-hydration force and, optionally, the electrostatic force of the solid support are tuned by pretreating the surface of the solid support, said pretreatment reducing the steric-hydration force such that the lipid vesicles rupture and form a stabilized bilayer membrane structure on the solid support, wherein the pretreatment is selected from the group consisting of thermal annealing, chemical titration, exposure to oxygen plasma, exposure to ultraviolet light, protonating functional groups on the surface of the solid support, a reducing agent, or treatment with a catalyst.

17. The method according to claim 1, wherein the steric-hydration force and, optionally, the electrostatic force of the solid support are tuned by pretreating the surface of the solid support, said pretreatment increasing the steric-hydration force such that adsorption of the lipid vesicles onto the solid support is inhibited, wherein the pretreatment is selected from the group consisting of chemical titration, exposure to oxygen plasma, exposure to ultraviolet light, deprotonating functional groups on the surface of the solid support, chemical titration, an oxidizing agent, or treatment with a catalyst.

18. A solid support comprising a stabilized lipid bilayer adsorbed thereon obtainable according to the method of claim 1.

19. A solid support resisting lipid vesicle adsorption thereon obtainable according to the method of claim 1.

* * * * *